US010551258B2

(12) United States Patent
Okita et al.

(10) Patent No.: US 10,551,258 B2
(45) Date of Patent: Feb. 4, 2020

(54) RESIDUAL STRESS ESTIMATION METHOD AND RESIDUAL STRESS ESTIMATION DEVICE (71) Applicant: KOBE STEEL, LTD., Hyogo (JP)

(72) Inventors: Keisuke Okita, Hyogo (JP); Tomokazu Nakagawa, Tokyo (JP); Mariko Yamada, Hyogo (JP)

(73) Assignee: Kobe Steel, Ltd., Hyogo (JP)

( * ) Notice: Subject to any disclaimer, the term of this patent is extended or adjusted under 35 U.S.C. 154(b) by 288 days.

(21) Appl. No.: 15/553,261

(22) PCT Filed: Feb. 22, 2016

(86) PCT No.: PCT/JP2016/055059
§ 371 (c)(1),
(2) Date: Aug. 24, 2017

(87) PCT Pub. No.: WO2016/140091
PCT Pub. Date: Sep. 9, 2016

(65) Prior Publication Data
US 2018/0045592 A1 Feb. 15, 2018

(30) Foreign Application Priority Data
Mar. 5, 2015 (JP) ................... 2015-043082

(51) Int. Cl.
G06G 7/48 (2006.01)
G01L 5/00 (2006.01)
(Continued)

(52) U.S. Cl.
CPC ............ G01L 5/0047 (2013.01); G01N 3/066 (2013.01); G01M 15/00 (2013.01); G01N 2203/0019 (2013.01); G01N 2203/0075 (2013.01)

(58) Field of Classification Search
CPC ...................................................... G01L 5/0047
(Continued)

(56) References Cited

U.S. PATENT DOCUMENTS
2011/0213594 A1 9/2011 Zhang

FOREIGN PATENT DOCUMENTS
CN 102152016 A 8/2011
JP H05-223661 A 8/1993
(Continued)

OTHER PUBLICATIONS
Extended European Search Report issued by the European Patent Office dated Oct. 4, 2018, which corresponds to EP16758785.6-1001 and is related to U.S. Appl. No. 15/553,261; 9 pp.
(Continued)

Primary Examiner — Hugh M Jones
(74) Attorney, Agent, or Firm — Studebaker & Brackett PC (57) ABSTRACT Provided is a residual stress estimation method and a residual stress estimation device capable of suppressing the number of cut pieces to be collected for measuring inherent strain without deteriorating residual stress estimation accuracy. In a case where it is assumed that the inherent strain is uniformly distributed in one direction in a structure, a user measures residual stress from a cut piece collected in a region in which the inherent strain is uniformly distributed and inputs the measured value to the residual stress estimation device. The residual stress estimation device estimates a two-dimensional inherent strain distribution on an analysis surface perpendicular to the one direction in the structure using the input residual stress measured value, transfers the estimated two-dimensional inherent strain distribution to the one direction, and estimates a three-dimensional inherent strain distribution in the structure.

8 Claims, 8 Drawing Sheets (51) Int. Cl.
*G01N 3/06* (2006.01)
*G01M 15/00* (2006.01)

(58) Field of Classification Search
USPC .............................................................. 703/7
See application file for complete search history.

(56) References Cited

FOREIGN PATENT DOCUMENTS

| | | |
|---|---|---|
| JP | 2003-121273 A | 4/2003 |
| JP | 2005-181172 A | 7/2005 |

OTHER PUBLICATIONS

International Search Report issued in PCT/JP2016/055059; dated May 17, 2016, 5 pp.
Written Opinion issued in PCT/JP2016/055059; dated May 17, 2016, 7 pp.
Mehdi Ghanadi; "Managing distortion in welded structures using FEM"; KTH Engineering Sciences; Jan. 1, 2013; pp. 1-36; Stockholm, Sweden.
Wei Liang et al.; "Predicting Welding Distortion in a Panel Structure with Longitudinal Stiffeners Using Inherent Deformations Obtained by Inverse Analysis Method"; The Scientific World Journal; Sep. 3, 2014; 8 pages; vol. 2014, Article ID 601417.

RESIDUAL STRESS ESTIMATION METHOD AND RESIDUAL STRESS ESTIMATION DEVICE

TECHNICAL FIELD

The present invention relates to a residual stress estimation method and a residual stress estimation device for estimating residual stress of a structure based on an inherent strain method.

BACKGROUND ART

Residual stress generated in a structure causes damage such as fatigue cracks in some cases and it is important to accurately grasp the distribution of the residual stress in the structure. As a method of estimating the residual stress of a structure, there has been known a method using an inherent strain method (for example, refer to Patent Documents 1 and 2).

In the method of estimating residual stress based on the inherent strain method of the related art, two kinds of cut pieces are cut out from a structure, the elastic strain or residual stress of each cut piece measured is measured, and the measured value of the elastic strain or residual stress of each cut piece is applied to inverse analysis processing based on a finite element method. In the inverse analysis processing, inherent strain is approximated with a least squares method using a distribution function and a distribution of inherent strain in the structure is determined, thereby calculating the residual strain of the structure before cutting from the obtained inherent strain distribution.

Patent Document 1 discloses that cut pieces of a T piece and an L piece are cut out from a test piece of a structure, and the respective T piece and L piece are further cut and divided into a plurality of small pieces to measure elastic (released) strain.

CITATION LIST

Patent Reference

Patent Document 1: JP-A-2005-181172
Patent Document 2: JP-A-2003-121273

SUMMARY OF THE INVENTION

Problems that the Invention is to Solve

The work for collecting a cut piece from a structure is very complicated and costs and working time also increase. When the number of cut pieces to be measured increases, shape errors, processing errors, and measurement errors are easily incorporated, which causes deterioration in residual stress estimation accuracy. On the other hand, when the number of cut pieces to be collected is too small, the number of measurement of elastic strain or residual stress is not sufficient and thus the residual stress of the structure cannot be estimated with high accuracy.

The present invention is made in consideration of the above circumstances and a primary object thereof is to provide a residual stress estimation method and a residual stress estimation device that can solve the above problems.

Means for Solving the Problems

In order to solve the above-described problems, a residual stress estimation method according to an aspect of the present invention includes steps of obtaining a measured value related to residual stress measured from a cut piece collected in a region in which the inherent strain is uniformly distributed in a case where it is assumed that the inherent strain is uniformly distributed in one direction in a structure; estimating a two-dimensional inherent strain distribution in a direction crossing the one direction in the structure based on the obtained measured value; and estimating a three-dimensional inherent strain distribution in the structure such that the estimated two-dimensional inherent strain distribution continues in the one direction.

In the aspect, in the step of obtaining a measured value, elastic strain or residual stress measured on a cut surface of the cut piece that is cut in the direction crossing the one direction may be obtained as the measured value.

In the aspect, in the step of estimating a three-dimensional inherent strain distribution, in a three-dimensional model of the structure in which a plurality of calculation points are three-dimensionally arranged, the estimated inherent strain value at each calculation point on one surface crossing the one direction may be given to each calculation point on the other surface crossing the one direction.

In the aspect, in the step of estimating a three-dimensional inherent strain distribution, when a calculation point to which the estimated inherent strain value is not given is present on the other surface, in a case where the one surface is overlapped with the other surface, the inherent strain at the calculation point may be compensated based on the inherent strain of the one surface around the calculation point to which the estimated inherent strain value is not given.

In the aspect, in the step of estimating a three-dimensional inherent strain distribution, a searching region may be set around the calculation point, and in a case where the calculation point of the one surface overlapped with the other surface is present in the searching region, the inherent strain at the calculation point to which the inherent strain is not given may be compensated based on the estimated inherent strain value at the calculation point of the one surface in the searching region.

In the aspect, in the step of estimating a three-dimensional inherent strain distribution, in a case where the calculation point of the one surface overlapped with the other surface is not present in the searching region, a searching region larger than the searching region may be newly set.

A residual stress estimation device according to the other aspect of the present invention includes: an input unit that receives, in a case where it is assumed that inherent strain is uniformly distributed in one direction in a structure, an input of a measured value related to residual stress measured from a cut piece collected in a region in which the inherent strain is uniformly distributed;

a first estimation unit of estimating a two-dimensional inherent strain distribution in a direction crossing the one direction in the structure based on the measured value received by the input unit;

a second estimation unit of estimating a three-dimensional inherent strain distribution in the structure such that the two-dimensional inherent strain distribution estimated by the first estimation unit continues in the one direction; and a display unit that displays a residual stress estimation result based on the three-dimensional inherent strain distribution estimated by the second estimation unit.

Advantages of the Invention

According to the present invention, it is possible to suppress the number of cut pieces to be collected for measuring elastic strain or residual stress without deteriorating residual stress estimation accuracy.

MODES FOR CARRYING OUT THE INVENTION

Hereinafter, preferred embodiments of the present invention will be described with reference to the drawings.

A residual stress estimation device according to the present invention is provided for, in a case where it is assumed that inherent strain is uniformly distributed in one direction, estimating a two-dimensional inherent strain distribution on a surface of a structure perpendicular to one direction, transferring the estimated two-dimensional inherent strain distribution to the other surface perpendicular to one direction, estimating a three-dimensional inherent strain distribution in the structure, and estimating residual stress of the structure based on the three-dimensional inherent strain distribution.

[Configuration of Residual Stress Estimation Device]

Figure 1:
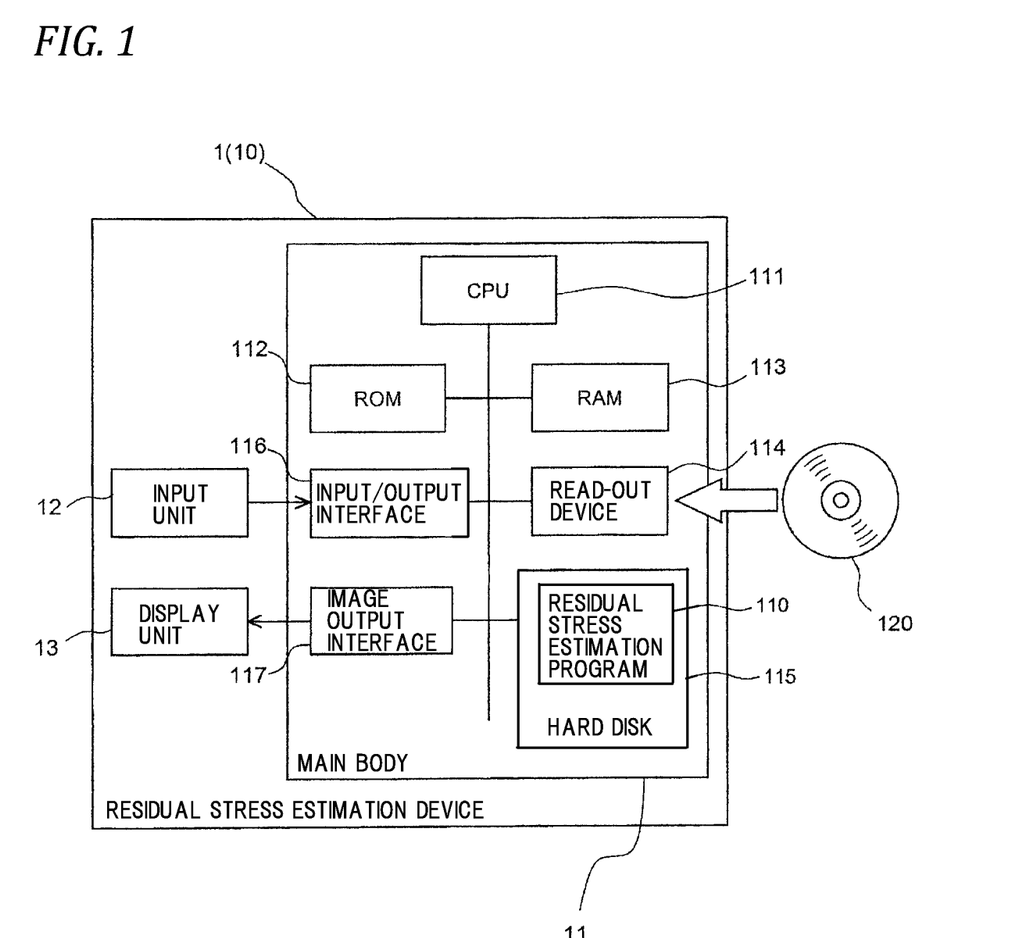
FIG. 1 is a block diagram illustrating a configuration of an embodiment of a residual stress estimation device according to the present invention.

A residual stress estimation device 1 is realized by a computer 10. As shown in FIG. 1, the computer 10 includes a main body 11, an input unit 12, and a display unit 13. The main body 11 includes a CPU 111, a ROM 112, a RAM 113, a hard disk 115, a read-out device 114, an input/output interface 116, and an image output interface 117, and the CPU 111, the ROM 112, the RAM 113, the hard disk 115, the read-out device 114, the input/output interface 116, and the image output interface 117 are connected by a bus.

The CPU 111 can execute a computer program loaded on the RAM 113. A residual stress estimation program 110 which is a computer program for residual stress estimation is executed by the CPU 111 and thus the computer 10 can function as the residual stress estimation device 1. The residual stress estimation program 110 is an inverse analysis process program based on a finite element method and a distribution state of inherent strain in the structure can be estimated.

The ROM 112 is configured by a mask ROM, a PROM, an EPROM, an EEPROM or the like and is recorded with the computer program to be executed by the CPU 111 and the data used for the same.

The RAM 113 is configured by an SRAM, a DRAM, and the like. The RAM 113 is used to read out the residual stress estimation program 110 recorded in the hard disk 115. When the CPU 111 executes the computer program, the RAM is used as a work region of the CPU 111.

The hard disk 115 is installed with various computer programs to be executed by the CPU 111 such as the operating system, the application program, and the like, and the data used for the execution of the relevant computer program. The residual stress estimation program 110 is also installed in the hard disk 115.

The hard disk 115 is installed with an operating system such as Windows (registered trademark) manufactured and sold by US Microsoft Co., for example. In the following description, the residual stress estimation program 110 according to the embodiment is assumed to operate on the operating system.

The read-out device 114 is configured by a flexible disk drive, a CD-ROM drive, a DVD-ROM drive, or the like, and can read out the computer program or the data recorded in a portable recording medium 120. The residual stress estimation program 110 is stored in the portable recording medium 120 to cause the computer to function as the residual stress estimation device. The computer 10 can read out the residual stress estimation program 110 from the portable recording medium 120 and install the residual stress estimation program 110 in the hard disk 115.

The input/output interface 116 is configured by, for example, a serial interface such as an USB, an IEEE 1394, or an RS-232C, or the like, a parallel interface such as an SCSI, an IDE, an IEEE 1284, or the like, and an analog interface including a D/A converter, an A/D converter, and the like. The input unit 12 including a keyboard and a mouse is connected to the input/output interface 116, and a user can input data to the computer 10 by using the input unit 12.

The image output interface 117 is connected to the display unit 13 configured by an LCD, a CRT, or the like, and a video signal according to the image data sent from the CPU 111 is output to the display unit 13. The display unit 13 displays an image (screen) according to the input video signal.

[Principle for Residual Stress Estimation Based on Inherent Strain Method]

(1) Calculation of Residual Stress Using Inherent Strain

When inherent strain is $\varepsilon_0$, residual stress $\sigma$ can be expressed by the following expression.

$$\sigma = D(\varepsilon - \varepsilon_0) \quad (1)$$

However, D represents an elastic coefficient matrix and $\varepsilon$ represents all strains satisfying the relation of the following expression.

[Equation 1]

$$\int B^T \sigma dV = \int B^T D(\varepsilon - \varepsilon_0) dV = 0 \quad (2)$$

Herein, $\int dV$ represents a volume fraction in the analysis region and B represents a coefficient matrix for relating a node displacement u and $\varepsilon$.

$$\varepsilon = Bu \quad (3)$$

In a case where the inherent strain is known, residual stress is obtained as follows.

The following expressions are given from Expressions (2) and (3).

[Equation 2]

$$Ku = P \quad (4)$$

Herein, $$K = \int B^T DB \, dV \quad (5)$$

$$P = \int B^T D\varepsilon_0 \, dV \quad (6)$$

K represents a rigidity matrix and P represents a load vector generated by the inherent strain.

When u is obtained by solving Expression (4), residual stress can be obtained from Expressions (3) and (1).

(2) Calculation of Inherent Strain Using Measured Residual Stress

N measured residual stress values are expressed as $\sigma_m$. Correspondingly, N calculated residual stress values obtained from the inherent strain are expressed as $\sigma_c$, and a residue R between the calculated residual stress and the measured residual stress is defined by the following expression.

[Equation 3]

$$R = (\sigma_m - \sigma_c)^T (\sigma_m - \sigma_c) \quad (7)$$

The inherent strain at an arbitrary point is expressed as the following linear function by M distribution function parameters a.

[Equation 4]

$$\varepsilon_0 = Ma \quad (8)$$

Herein, M represents a coordinate function and the coordinates may not be linear.

When the inherent strain is determined by Expression (8), the measured residual stress is obtained by the method of (1) above and as a result, a linear relation expression can be obtained as follows.

[Equation 5]

$$\sigma_c = Ha \quad (9)$$

Herein, H represents a coefficient matrix and the component thereof can be obtained by obtaining residual stress by giving a unit value to each component of a.

When a is determined such that R is the minimum by substituting Expression (9) into Expression (7), an inherent strain distribution in which an error between the measured residual stress and the calculated residual stress at the measurement point is the minimum is determined.

[Operation of Residual Stress Estimation Device]

Hereinafter, the operation of the residual stress estimation device 1 according to the embodiment will be described.

The residual stress estimation device 1 performs residual stress estimation processing as described below to estimate the residual stress of the structure.

Figure 2:
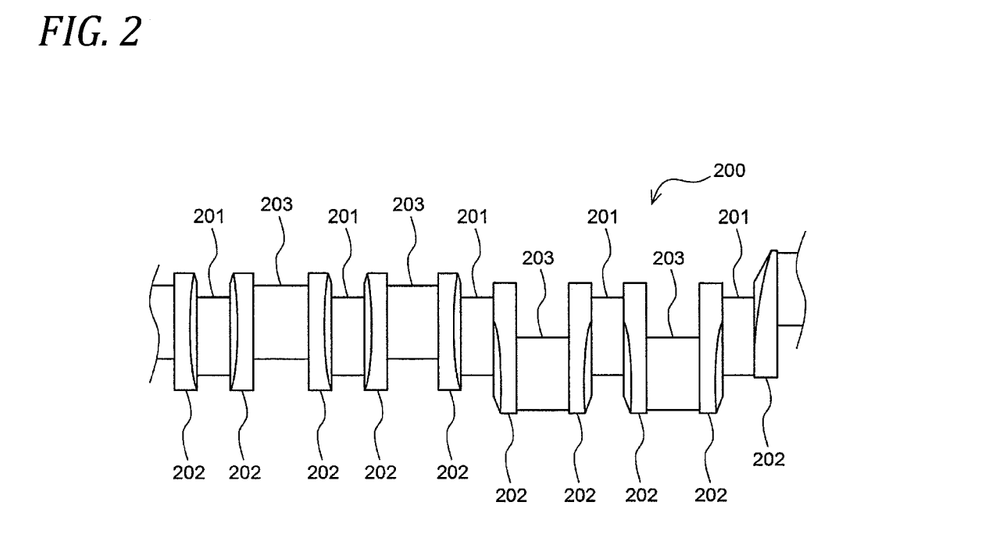
FIG. 2 is a side view illustrating a configuration of a crank shaft.

The structure is formed by plastic processing. Herein, a crank shaft will be described as an example of the structure. As shown in FIG. 2, a crank shaft 200 is configured such that a journal shaft 201 and a pin shaft 203 are connected by a crank arm 202. In the connection place of the journal shaft 201 and the crank arm 202 and the connection place of the pin shaft 203 and the crank arm 202, great stress is easily generated in use. When tension residual stress is easily generated in these connection places, damage such as fatigue cracks may be caused. In order to improve fatigue life, plastic processing such as roll processing or shot peening is performed on the connection places and compressive residual stress is introduced.

Figure 3:
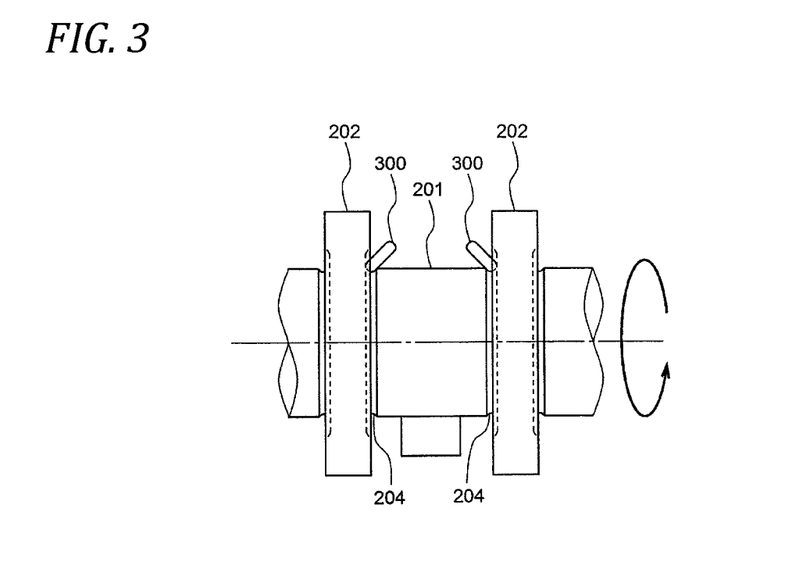
FIG. 3 is a side view illustrating plastic processing with respect to the crank shaft in an enlarged manner.

FIG. 3 is a diagram illustrating plastic processing with respect to the crank shaft. In FIG. 3, a case of roll processing is illustrated. In the roll processing, in a state in which a roll 300 is pressed against the connection place of the journal shaft 201 (or the pin shaft 203) and the crank arm 202, the journal shaft 201 is rotated. Thus, in the connection place, a fillet 204 is formed and compressive residual stress is applied such that the residual stress is uniformly distributed in the circumferential direction of the journal shaft 201.

Figure 4A:
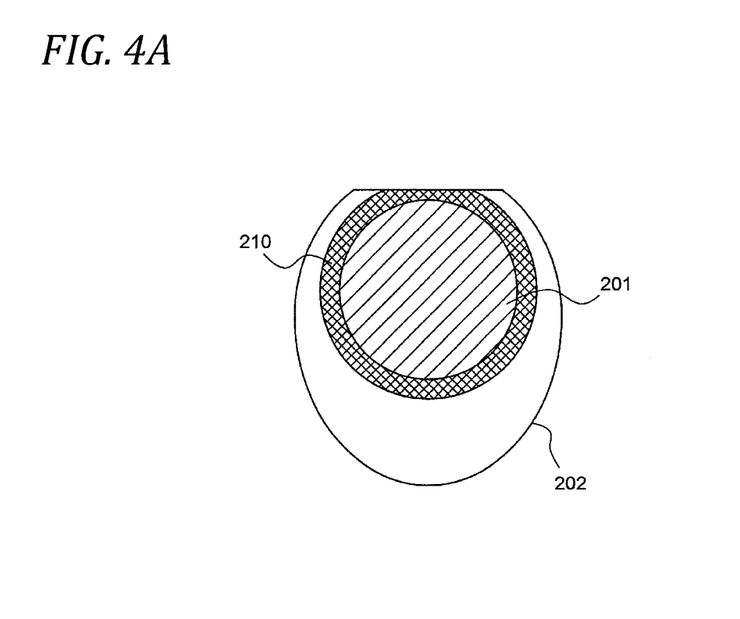
FIG. 4A is a cross-sectional view illustrating a processing range on a journal shaft.
Figure 4B:
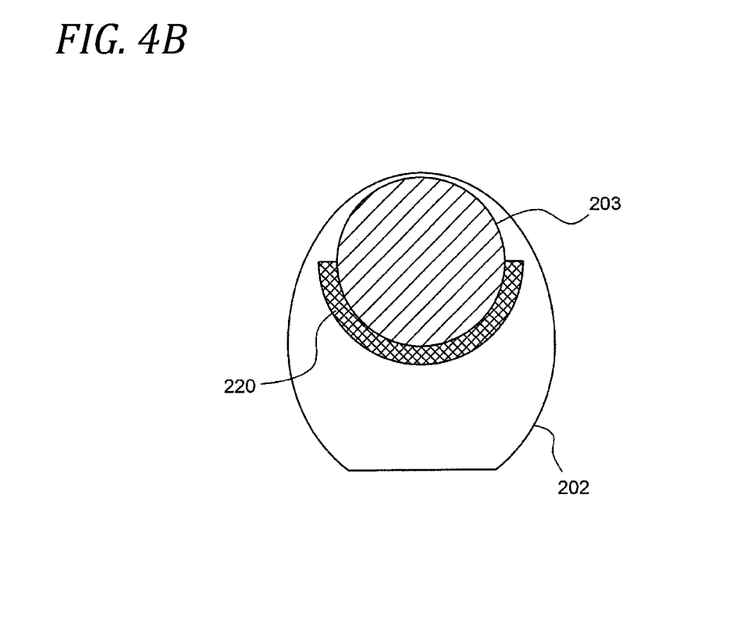
FIG. 4B is a cross-sectional view illustrating a processing range on a pin shaft.

The roll processing is performed over the whole circumference of the journal shaft 201 and is performed on a part of the pin shaft 203 in the circumferential direction. As shown in FIG. 4A, the roll processing is performed in a ring-shaped processing range 210 over the whole circumference of the journal shaft 201. Therefore, the filler 204 is formed over the whole circumference of the journal shaft 201. On the other hand, as shown in FIG. 4B, the roll processing is performed in a processing range 220 of 180° in the pin shaft 203. Therefore, the fillet 204 is formed in a range of 180° in the pin shaft 203.

Figure 5:
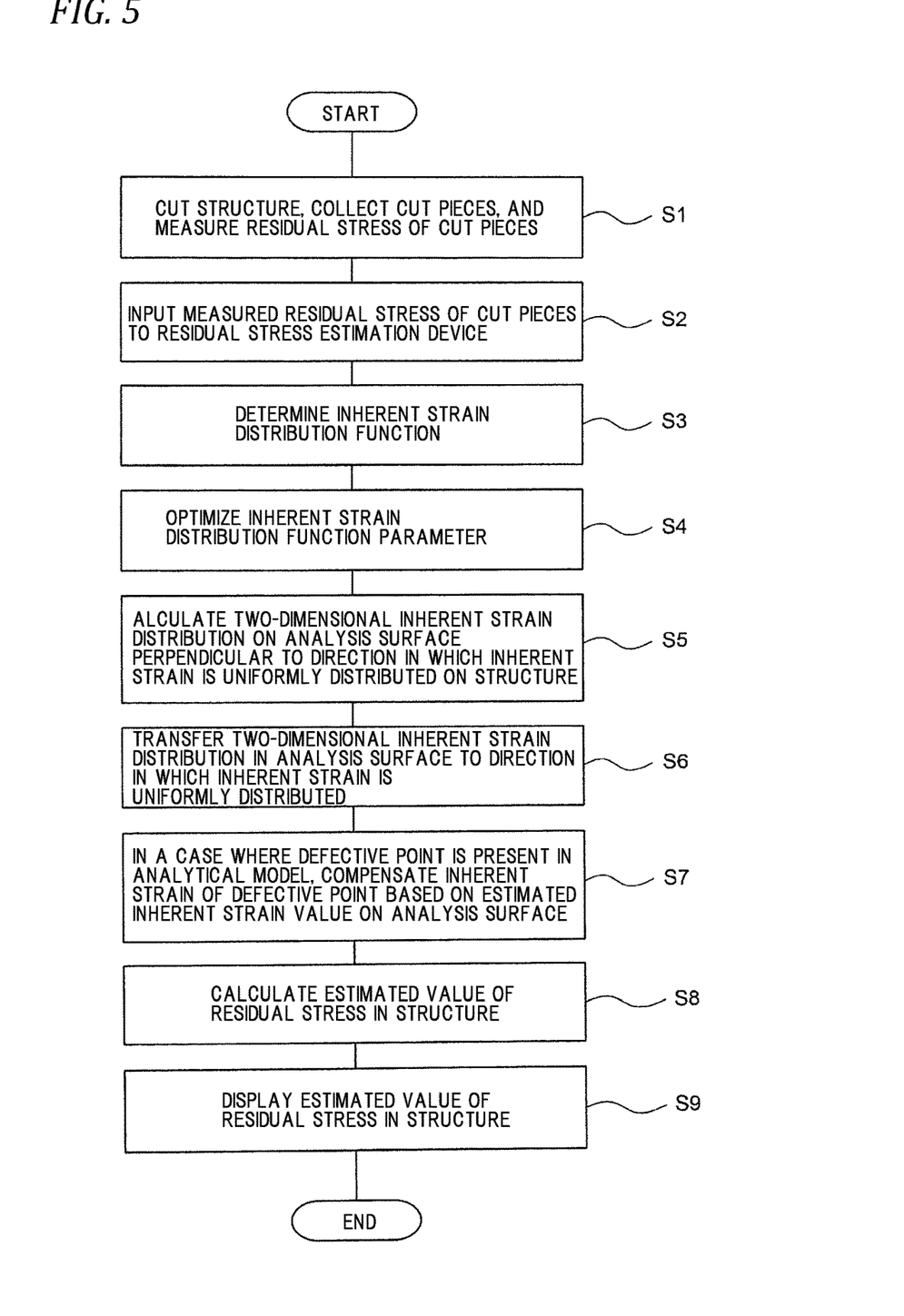
FIG. 5 is a flow chart illustrating the procedure of an embodiment of a residual stress estimation method according to the present invention.

As described above, the residual stress of the structure in which the compressive residual stress is uniformly applied in one direction is estimated using the residual stress estimation device 1. FIG. 5 is a flow chart illustrating the procedure of a residual stress estimation method according to an embodiment.

A user collects a cut piece by cutting the structure and measures the residual stress from the cut piece (Step S1). Specifically, the structure is thinly cut in one direction to collect a cut piece (T piece) and is cut in a direction perpendicular to the one direction to collect a cut piece (L piece).

Here, the residual stress is a value obtained by multiplying elastic strain by a Young's modulus, and measuring elastic strain is equivalent to measuring residual stress. Accordingly, either elastic strain or residual stress may be measured from the cut piece. In the embodiment, a case of measuring the residual stress will be described.

Figure 6:
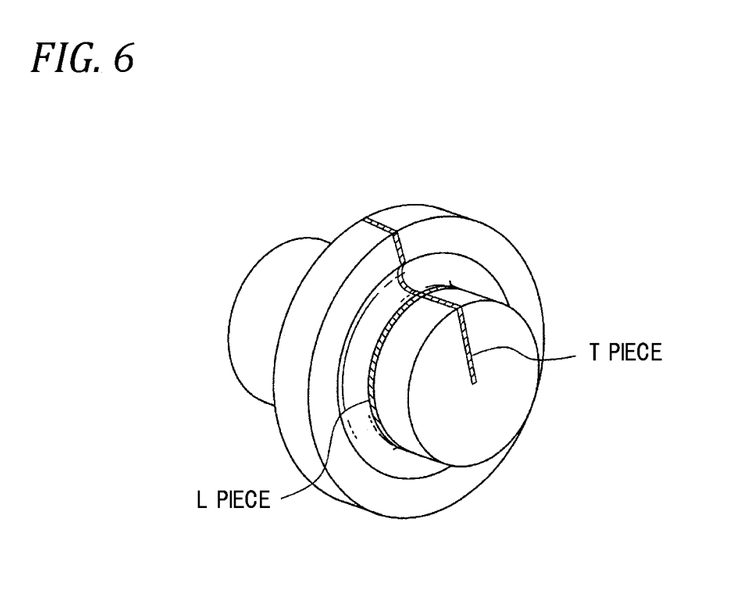
FIG. 6 is a perspective view illustrating examples of cut pieces collected from a structure.

As shown in FIG. 6, in a case of an axisymmetric structure, such as a journal shaft or a pin shaft, to which the compressive residual stress is uniformly applied in the circumferential direction, a T piece is obtained by cutting the structure in a radial direction. If the inherent strain is uniformly distributed in the circumferential direction, even in a case where a T piece is obtained from any portion in the circumferential direction, the inherent strain does not change. Accordingly, the T piece to be collected may be only one. Accordingly, the number of T pieces to be collected can be reduced.

Thus, it is possible to reduce the workload of the cutting processing and the measurement of the residual stress of the cut piece.

On the other hand, the inherent strain distribution in the shaft length direction is complicated. Accordingly, it is necessary to collect the L piece in a plurality of places in the shaft length direction.

Figure 7:
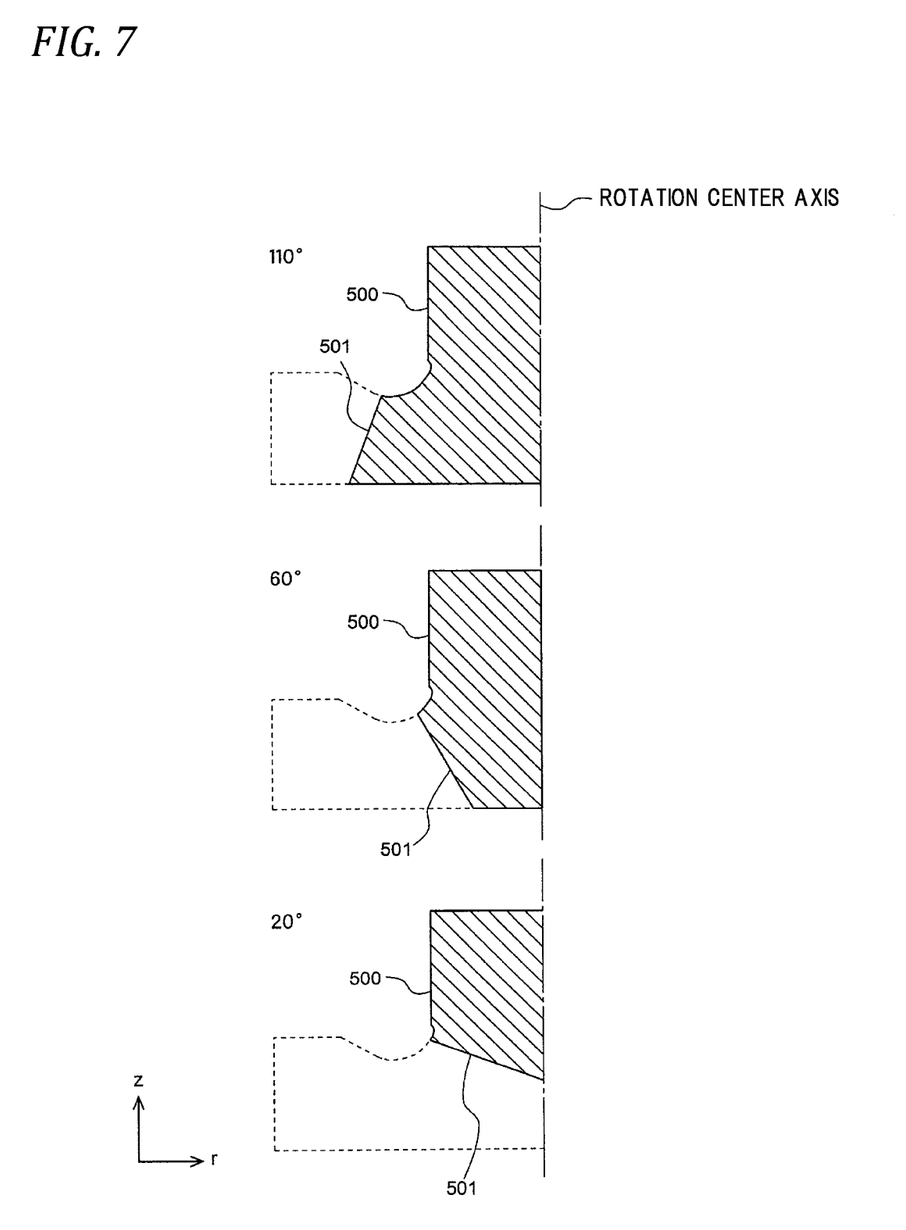
FIG. 7 is a cross-sectional view of the journal shaft for illustrating collection of a C piece.

In a case of having a bent surface like the fillet portion of the crank shaft, instead of the L piece, a conical cut piece (hereinafter, referred to as "C piece") cut in a direction normal to the bent surface may be collected. In addition, the L piece and the C piece are not collected and only the T piece may be collected. In FIG. 7, each view is a cross-sectional view when the journal shaft is cut in the rotation axis length direction. A C piece 500 is obtained by cutting the structure in a direction normal to the bent surface of the fillet, that is, in the radius direction of the arc-shaped fillet in the cross section. Since the journal shaft has an axisymmetric shape, a cross section 501 of the C piece 500 conically extends around the rotation center axis of the journal shaft. Several C pieces are collected by changing the central angle of the fillet (for example, from 20° to 110° at every 10°).

In a case where compressive residual stress is uniformly applied to a rod-like structure long in one direction in the longitudinal direction, only one T piece can be collected in one place in the longitudinal direction.

The user directly measures the residual stress of the cut piece collected as described above with X-rays or the like. In a case of measuring the elastic strain, the user attaches a strain gauge to the cut piece and further cuts the cut piece into a plurality of small pieces to measure released strain (elastic strain) of each small piece. In the measurement of the residual stress or released strain (elastic strain), a plurality of components that are different from each other are measured.

Figure 8:
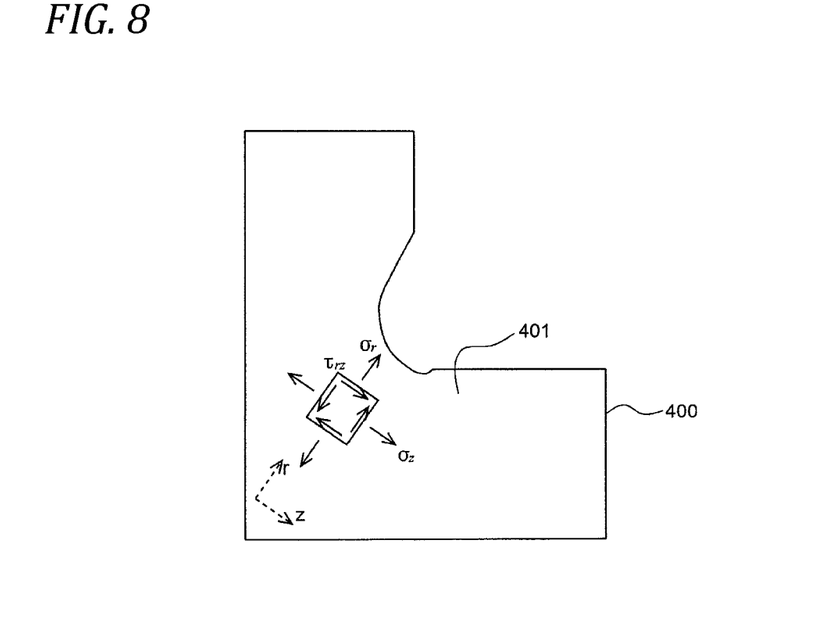
FIG. 8 is a schematic view illustrating an example of measurement of the residual stress of a cut piece.

FIG. 8 illustrates an example in which the residual stress of the T piece of the fillet portion of the journal shaft (or the pin shaft) is measured. A T piece 400 has a cross section 401 perpendicular to the circumferential direction of the journal shaft (or the pin shaft), and the user measures respective components $\sigma_r$ and $\alpha_z$ in an r direction and a z direction perpendicular to each other in the cross section 401. Generally, these two components are measured in the T piece and two direction components perpendicular to each other are also measured in the L piece (or the C piece).

FIG. 5 is referred to again. The user inputs the residual stress of the cut pieces to the residual stress estimation device 1. The CPU 111 of the residual stress estimation device 1 receives the residual stress of the cut pieces input from the input unit 12 (Step S2).

Next, the CPU 111 determines an inherent strain distribution function (Step S3). As the distribution function, an arbitrary multidimensional polynomial or a trigonometric series can be selected. In this case, the CPU 111 may automatically select the distribution function or the user may designate a desired distribution function by using the input unit 12. In the residual stress estimation device 1, the distribution function may be set in advance.

The distribution function determined in Step S3 is provided for estimating the inherent strain of the structure in which inherent strain is uniformly distributed in one direction. Specifically, the distribution function is a distribution function for expressing the two-dimensional inherent strain distribution of the cross section of the journal shaft (or the pin shaft) perpendicular to the circumferential direction. Accordingly, the distribution function for expressing the inherent strain distribution in the circumferential direction is not used.

Next, the CPU 111 optimizes the parameters of the distribution function (Step S4). Hereinafter, the processing of Step S4 will be described in detail.

The CPU 111 first determines H in Expression (9). The procedure thereof is as follows.

(a) $a=[1, 0, 0, \ldots, 0]^T$ is set and $\varepsilon_0 =Ma$ is obtained.
(b) Expression (4) is solved and u is obtained.
(c) $\varepsilon$ is obtained by Expression (3).
(d) $\sigma$ is obtained by Expression (1).
(e) N values corresponding to the residual stress measurement point are extracted from the components of a and the extracted values are set to a first column of H.
(f) $a=[0, 1, 0, \ldots, 0]^T$ is set and a second column of H is also obtained in the same procedure of (b) to (f).

Next, the CPU 111 determines "a" such that R of Expression (7) is the minimum. Accordingly, the distribution function parameters are optimized.

Further, the CPU 111 calculates a two-dimensional inherent strain distribution on an analysis surface perpendicular to a direction in which inherent strain is uniformly distributed in the structure (Step S5).

In the processing of Step S5, in a case where a portion of the crank shaft in which the pin shaft and the crank arm are connected to each other is set as a target to be analyzed, the surface of the pin shaft perpendicular to the circumferential direction becomes an analysis surface. The CPU 111 obtains inherent strain at an arbitrary point of the analysis surface by Expression (8).

Next, the CPU 111 transfers the two-dimensional inherent strain distribution on the calculated analysis surface to the circumferential direction (the direction in which inherent strain is uniformly distributed) (Step S6). At this time, in a case where the journal shaft is a target to be analyzed, the CPU 111 transfers the inherent strain in a range of 360°, and in a case where the pin shaft is a target to be analyzed, the CPU 111 transfers the inherent strain in a range of 180°. Accordingly, the inherent strain can be transferred in accordance with an actual processing range.

Figure 9:
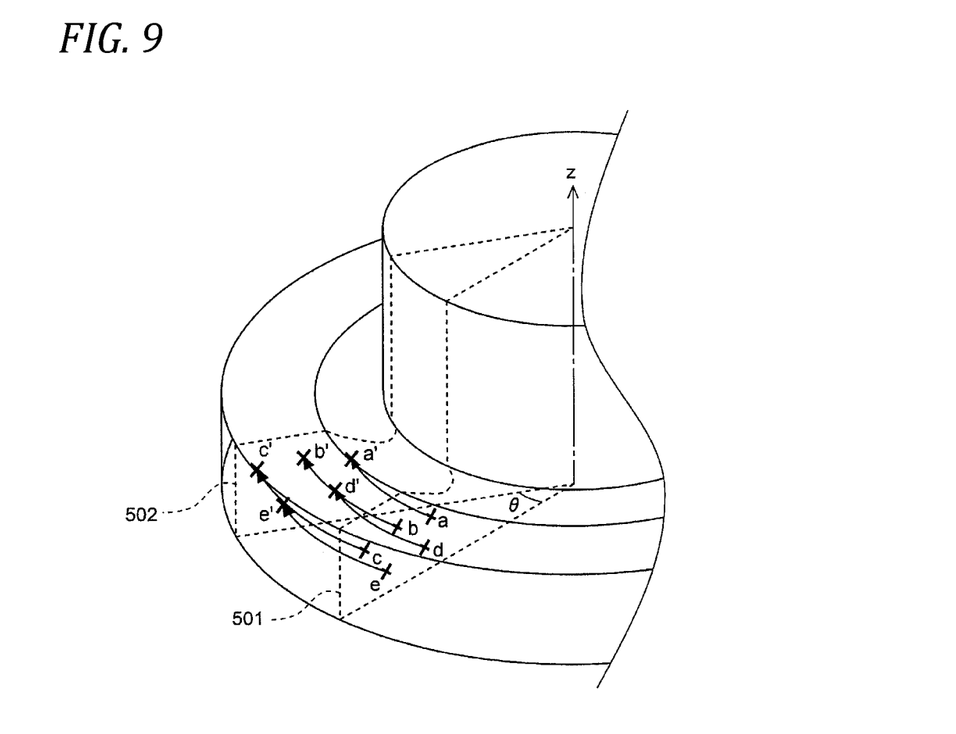
FIG. 9 is a perspective view illustrating transfer of inherent strain to a circumferential direction on an analysis surface.

As shown in FIG. 9, the processing of Step S6 is performed on a three-dimensional model (analytical model) of a structure built in a virtual three-dimensional space. The analytical model is constituted by arranging a plurality of three-dimensional elements (a tetrahedron, a hexahedron, or the like). Herein, the calculation point is placed at the center point of the three-dimensional element. In FIG. 9, at the respective calculation points a to e on the analysis surface 501, inherent strain estimated values are given. A case where the inherent strain is transferred to a transfer surface 502 spaced from the analysis surface 501 by θ around a z axis which is the rotation center is considered. The CPU 111 transfers the respective estimated inherent strain values at the calculation points a to e to calculation points a' to e' corresponding to the calculation points a to e on the transfer surface. That is, the inherent strain values at the calculation points a' to e' are the same as the respective inherent strain values at the calculation points a to e. The CPU 111 performs such processing over the transfer range (in a case of the journal shaft, in a range of 360°, and in a case of the pin shaft, in a range of 180°).

In a case where the target to be analyzed is a structure in which compressive stress is uniformly applied in a liner direction, the CPU 111 transfers the two-dimensional inherent strain distribution on the analysis surface perpendicular to the liner direction to the linear direction.

Next, in a case where a point to which the inherent strain is not transferred (hereinafter, referred to as "defective point") is present in the analytical model, the CPU 111 compensates the inherent strain of the defective point (Step S7).

Figure 10:
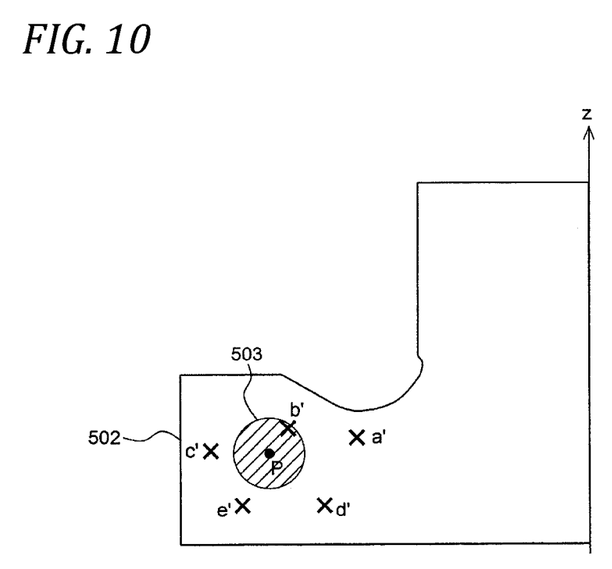
FIG. 10 is a schematic view illustrating compensation of the inherent strain on a transfer surface.

The processing of Step S7 will be described using FIG. 10. In FIG. 10, in a case where the calculation point P on the transfer surface 502 is the defective point, the CPU 111 sets a circular searching region 503 around the defective point P.

The CPU 111 determines whether or not the calculation point of the analysis surface 501 is present in the searching region 503 when the analysis surface 501 is overlapped with the analysis surface 502 by moving the analysis surface 501 around the z axis by θ. In a case where the calculation point of the analysis surface 501 is present in the searching region 503, the CPU 111 compensates the inherent strain at the defective point from the estimated inherent strain value at the calculation point thereof. In the compensation of the inherent strain, a known interpolation method, extrapolation method, or other estimation methods can be used. For example, the estimated inherent strain value at the nearest calculation point of the defective point can be set as an estimated inherent strain value at the defective point (nearest neighbor interpolation). In a case of searching two or more calculation points, spline interpolation, polynomial interpolation, linear interpolation, and the like (the same is applied to the extrapolation method) may be used and the estimated inherent strain value at each calculation point may be averaged.

In the processing of Step S7, at least one calculation point may be searched and a plurality of calculation points may be searched.

In a case where the calculation point of the analysis surface 501 is not present in the searching region 503, the CPU 111 sets a new searching region one size larger than the searching region to search the calculation point. Subsequently, the CPU 111 sets a searching region that is gradually increased until the calculation point is searched.

When the inherent strains of all the defect points are compensated in Step S7, the CPU 111 calculates a residual stress estimated value (Step S8).

In the processing of Step S8, the CPU 111 obtains u by solving Expression (4) from the inherent strain at each point and the obtained u is applied to Expression (3) to obtain ε. Then, the obtained ε is applied to Expression (1) to obtain σ.

Next, the CPU 111 displays the obtained residual stress estimated value on the display unit 13 (Step S9).

After Step S9, the CPU 111 ends the processing.

By adopting the above-described configuration, regarding the structure in which residual stress is uniformly distributed in one direction (the circumferential direction around the shaft, the linear direction, or the like), the number of cut pieces to be collected for measuring inherent strain can be reduced without deteriorating residual stress estimation accuracy.

Other Embodiments

In the above-described embodiment, the estimation of the residual stress in the structure which is subjected to plastic processing is described but the present invention is not limited thereto. Processing such as welding or heat treatment other than plastic processing is performed and the residual stress in the structure in which inherent strain is uniformly present in one direction can be also estimated in the same manner.

In the above-described embodiment, the configuration in which the residual stress is measured from the cut piece of the structure and the parameter of the distribution function is optimized such that a difference between the measured residual stress and the residual stress calculated by the distribution function is the minimum is described, but the present inversion is not limited thereto. A configuration in which the released strain (elastic strain) is measured from the cut piece of the structure and the parameter of the distribution function is optimized such that a difference between the measured released strain and the elastic strain calculated by the distribution function is the minimum may be adopted.

INDUSTRIAL APPLICABILITY

The residual stress estimation method and the residual stress estimation device of the present invention are a residual stress estimation method and a residual stress estimation device for estimating the residual stress of a structure based on an inherent strain method.

The present application is based on Japanese Patent Application (Patent Application No. 2015-043082) filed on Mar. 5, 2015, the contents of which are incorporated herein by reference.

DESCRIPTION OF REFERENCE NUMERALS AND SIGNS

1: Residual stress estimation device
10: Computer
12: Input unit
13: Display unit
110: Residual stress estimation program
111: CPU
115: Hard disk
116: Input/output interface
117: Image output interface
200: Crank shaft (structure)
400: T piece (cut piece)
401: Cross section
500: C piece (cut piece)
501: Cross section
503: Searching region

The invention claimed is:

1. A residual stress estimation method based on inherent strain for use in suppressing deformation during plastic processing, the residual stress estimation method comprising steps of:
    obtaining a measured value related to residual stress measured from a cut piece collected in a region in which the inherent strain is uniformly distributed in a case where it is assumed that the inherent strain is uniformly distributed in one direction in a structure;
    estimating a two-dimensional inherent strain distribution in a direction crossing the one direction in the structure based on the obtained measured value;
    estimating a three-dimensional inherent strain distribution in the structure such that the estimated two-dimensional inherent strain distribution continues in the one direction; and
    optimizing processing conditions of the structure based on the estimated three-dimensional inherent strain distribution to thereby suppress deformation of the structure resulting from the inherent strain.

2. The residual stress estimation method according to claim 1, wherein in the step of obtaining a measured value, elastic strain or residual stress measured on a cut surface of the cut piece that is cut in the direction crossing the one direction is obtained as the measured value.

3. The residual stress estimation method according to claim 2,
    wherein in the step of estimating a three-dimensional inherent strain distribution, in a three-dimensional model of the structure in which a plurality of calculation points are three-dimensionally arranged, the estimated inherent strain value at each calculation point on one surface crossing the one direction is given to each calculation point on the other surface crossing the one direction.

4. The residual stress estimation method according to claim 1,
    wherein in the step of estimating a three-dimensional inherent strain distribution, in a three-dimensional model of the structure in which a plurality of calculation points are three-dimensionally arranged, the estimated inherent strain value at each calculation point on one surface crossing the one direction is given to each calculation point on the other surface crossing the one direction.

5. The residual stress estimation method according to claim 4,
wherein in the step of estimating a three-dimensional inherent strain distribution, when a calculation point to which the estimated inherent strain value is not given is present on the other surface, in a case where the one surface is overlapped with the other surface, the inherent strain at the calculation point is compensated based on the inherent strain of the one surface around the calculation point to which the estimated inherent strain value is not given.

6. The residual stress estimation method according to claim 5,
wherein in the step of estimating a three-dimensional inherent strain distribution, a searching region is set around the calculation point, and in a case where the calculation point of the one surface overlapped with the other surface is present in the searching region, the inherent strain at the calculation point to which the inherent strain is not given is compensated based on the estimated inherent strain value at the calculation point of the one surface in the searching region.

7. The residual stress estimation method according to claim 6,
wherein in the step of estimating a three-dimensional inherent strain distribution, in a case where the calculation point of the one surface overlapped with the other surface is not present in the searching region, a searching region larger than the searching region is newly set.

8. A residual stress estimation device for use in suppressing deformation during plastic processing, the residual stress estimation device comprising:
an input unit that receives, in a case where it is assumed that inherent strain is uniformly distributed in one direction in a structure, an input of a measured value related to residual stress measured from a cut piece collected in a region in which the inherent strain is uniformly distributed;
a first estimation unit that estimates a two-dimensional inherent strain distribution in a direction crossing the one direction in the structure based on the measured value received by the input unit;
a second estimation unit that estimates a three-dimensional inherent strain distribution in the structure such that the two-dimensional inherent strain distribution estimated by the first estimation unit continues in the one direction;
a display unit that displays a residual stress estimation result based on the three-dimensional inherent strain distribution estimated by the second estimation unit; and
a processor that optimizes processing conditions of the structure based on the estimated three-dimensional inherent strain distribution to thereby suppress deformation of the structure resulting from the inherent strain.

* * * * *